US012419516B2

(12) United States Patent
Enten et al.

(10) Patent No.: US 12,419,516 B2
(45) Date of Patent: Sep. 23, 2025

(54) CAPTURING DIAGNOSABLE VIDEO CONTENT USING A CLIENT DEVICE

(71) Applicant: Insight Optics, Inc., Brier, WA (US)

(72) Inventors: Aaron Christopher Enten, Brier, WA (US); Theodore J. LaGrow, Atlanta, GA (US)

(73) Assignee: Insight Optics, Inc., Brier, WA (US)

( * ) Notice: Subject to any disclaimer, the term of this patent is extended or adjusted under 35 U.S.C. 154(b) by 816 days.

(21) Appl. No.: 17/586,491

(22) Filed: Jan. 27, 2022

(65) Prior Publication Data

US 2023/0144621 A1 May 11, 2023

Related U.S. Application Data

(60) Provisional application No. 63/278,446, filed on Nov. 11, 2021.

(51) Int. Cl.
| | | |
|---|---|---|
| A61B 3/14 | (2006.01) | |
| A61B 3/113 | (2006.01) | |
| G06N 3/045 | (2023.01) | |
| G06T 7/00 | (2017.01) | |
| G06V 20/40 | (2022.01) | |
| G16H 10/60 | (2018.01) | |
| G16H 40/67 | (2018.01) | |

(52) U.S. Cl.
CPC .............. *A61B 3/145* (2013.01); *A61B 3/113* (2013.01); *G06N 3/045* (2023.01); *G06T 7/0002* (2013.01); *G06V 20/46* (2022.01); *G16H 10/60* (2018.01); *G16H 40/67* (2018.01); *G06T 2207/30168* (2013.01)

(58) Field of Classification Search
CPC ........... A61B 3/145; A61B 3/113; A61B 3/12; A61B 3/0025; G06N 3/045; G06T 7/0002; G06T 2207/30168; G06T 7/30; G06T 2207/20084; G06T 7/0012; G06T 2207/10016; G06T 2207/30041; G06V 20/46; G06V 10/809; G06V 10/82; G06V 10/993; G06V 40/193; G16H 10/60; G16H 40/67; G16H 80/00; G16H 30/40; G16H 50/20
USPC .......................................................... 351/206
See application file for complete search history.

(56) References Cited

U.S. PATENT DOCUMENTS

| | | | | |
|---|---|---|---|---|
| 2018/0005666 | A1* | 1/2018 | Yang | G11B 27/326 |
| 2021/0307864 | A1* | 10/2021 | Wolf | G11B 27/34 |
| 2022/0092776 | A1* | 3/2022 | Ehlers | G06T 7/0012 |
| 2022/0095911 | A1* | 3/2022 | DeAyala | A61B 3/0025 |

\* cited by examiner

*Primary Examiner* — Bumsuk Won
*Assistant Examiner* — Rahman Abdur
(74) *Attorney, Agent, or Firm* — Ray Quinney & Nebeker P.C.; James S. Bullough

(57) ABSTRACT

A system for providing remote healthcare includes receiving a video captured on a mobile device. An image quality assessor analyzes the video to provide a video quality score to the PCP in real time while the PCP is still meeting with the patient. The image quality assessor applies an ensemble neural net to identify anatomical features in the captured video.

19 Claims, 12 Drawing Sheets

CAPTURING DIAGNOSABLE VIDEO CONTENT USING A CLIENT DEVICE

CROSS-REFERENCE TO RELATED APPLICATIONS

This application claims the benefit of U.S. Provisional Patent Application No. 63/278,446, filed on Nov. 11, 2021, which is hereby incorporated by reference in its entirety.

BACKGROUND

Recent years have seen improvements in remote health care. For example, health care professionals may receive health data about a patient even where a health care professional is located remotely from the patient. Using the remotely received physiological information, the health care professional may provide health care advice to the user, such as a diagnosis, a prescription, instructions for care, and so forth. Providing and receiving regular medical care, however, suffers from a number of drawbacks and limitations.

For example, many patients are reticent to visit a specialist health care provider. Many patients may not be comfortable with a specialist, may be intimidated by a specialist, may not have time for multiple health care appointments, may live too far away from a specialist, may not visit a specialist for any other reasons, or have other circumstances that prevent in-person visits to specialists. This may result in patients that do not receive life-improving and/or life-saving health care because they are unable or unwilling to visit a particular specialist. While remote health care has helped to alleviate some of these concerns, a remote specialist may not be able to provide medical advice if he or she does not receive health information of diagnosable quality for the user.

In some situations, the physiological and other health information received by the remote health care professional may not be of diagnosable quality. For example, the physiological information may not include sufficient detail, and the remote health care professional may not have enough information to provide health care advice. In some examples, the physiological information may include images that are blurry, too bright, not bright enough, or otherwise of low quality. If the remote health care professional does not have diagnosable quality physiological information, the patient may have to provide additional information by way of an in-person or follow up visit. However, patient compliance for additional requests for information may be low, resulting in reduced health care for the user.

In some situations, the physiological information may be collected using specialized imaging devices or other specialized machines. While specialized imaging devices or high-end machinery may reliably generate high quality images or other physiological information, these specialized imaging devices or machines may require an operator to have special training and/or qualifications. Furthermore, such specialized imaging devices or machines may be prohibitively expensive for a primary care provider (PCP) or other non-specialist to own and/or operate.

In some situations, a PCP, patient, or other individual may collect the physiological information for the user using conventional tools available to him or her. For example, where a PCP is a general practitioner and a remote health care professional is a specialist, the PCP may prepare and send the physiological information to the remote specialist. However, because the PCP is generally not a specialist, the PCP may not know what information to collect and/or what information the specialist may find important. Furthermore, the PCP may not have the specialized equipment used to generate high quality physiological information. This may further result in delays to the patient in receiving important advice from the remote specialist and/or require return trips from the patient.

These and other difficulties exist in capturing physiological information of a diagnosable quality for use by a health care professional in providing important medical advice to remote clients.

BRIEF DESCRIPTION OF THE DRAWINGS

The detailed description provides one or more embodiments with additional specificity and detail through the use of the accompanying drawings, as briefly described below.

DETAILED DESCRIPTION

Figure 1:
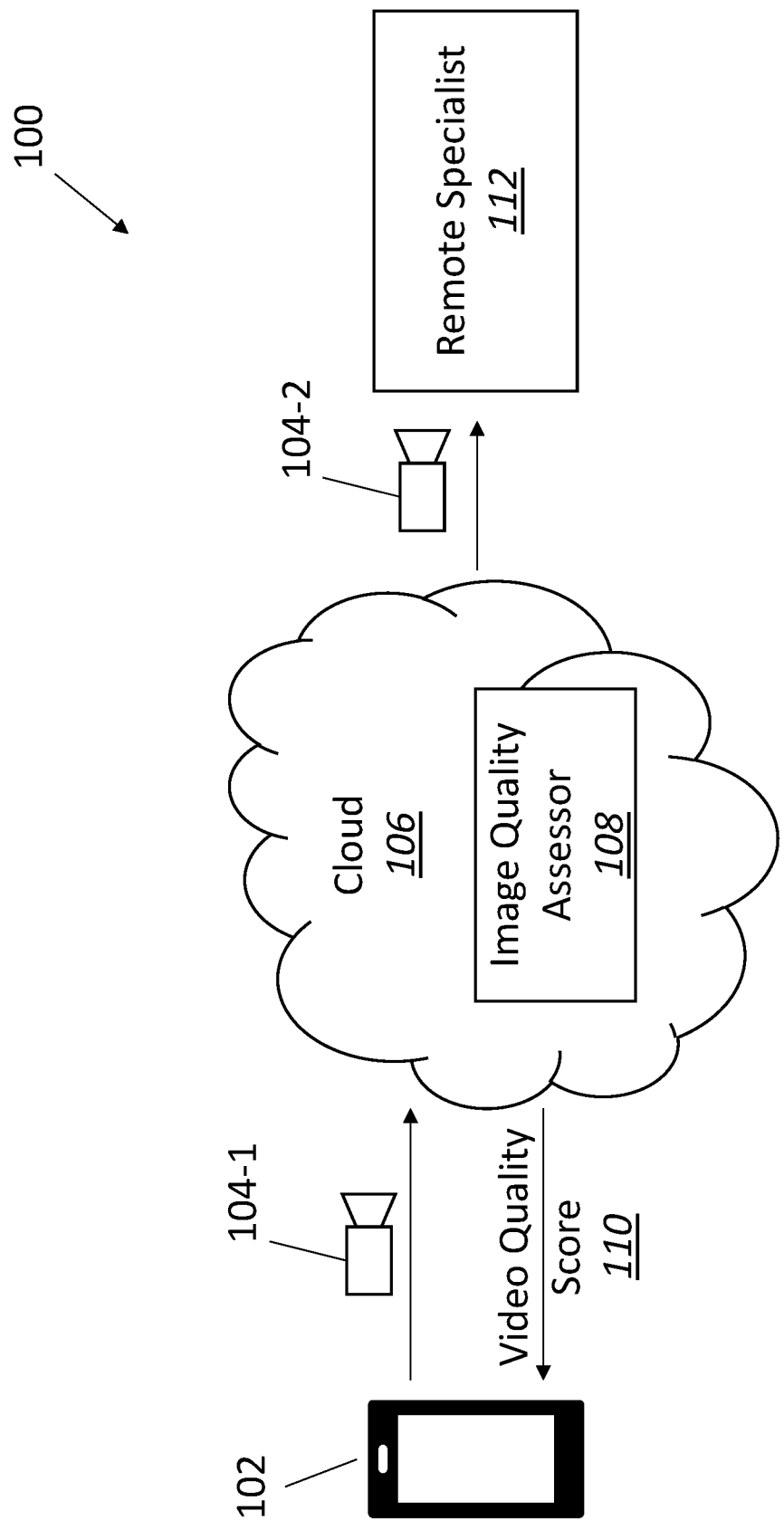
FIG. 1 illustrates a diagram of an environment in which a remote healthcare system can operate in accordance with one or more embodiments.

This application relates to devices, systems, methods, and computer-readable media for providing digital content (e.g., image content, video content) of diagnosable quality to a remote health care professional, such as a remote ophthalmologist who may provide remote diagnoses for eye diseases. A local primary care provider (PCP), such as an optometrist, may collect video content of an interior of a patient's eye using a smartphone camera connected to an ophthalmoscope. The optometrist may transmit the video to a cloud server. The cloud server may perform an image quality assessment (IQA) of the video. The IQA may include utilizing an ensemble neural network (or simply an "ensemble neural net" or a "neural net") to analyze the frames of the video for the presence of features of the eye, including the optic nerve, the macula, vasculature, and other structures. The cloud server may then transmit to the PCP's mobile device an image quality score of one or more frames or selective segments of the video and/or a video quality score of the entire captured video. The optometrist may review the image quality score and determine whether to re-record the video or send it on to a specialist. The ophthalmologist may then review the video and provide medical advice based on the information contained within the video content.

In accordance with embodiments of the present disclosure, an image quality assessor at the cloud server may perform the IQA. The image quality assessor may receive the eye exam video from the mobile device of the PCP and analyze the video against predetermined metrics, such as the presence of the optic nerve, the macula, and/or vasculature. The image quality assessor may determine a video quality score for the eye exam video based on the comparison of the captured video against the predetermined metrics. Based on the video quality score, the image quality assessor may provide an indication to the mobile device (and thus the PCP) whether the captured video is suitable for use in a remote medical application.

In some embodiments, the image quality assessor may receive an eye exam video from a mobile device. The image quality assessor may analyze each frame of the eye exam video for the presence of one or more ocular features, such as the optic nerve, the macula, or vasculature. In some embodiments, the image quality assessor may utilize one or multiple quality analysis models to perform the analysis of the frames of the video. In some embodiments, the image quality assessor may select a plurality of frames from the video based on detected presence of one or more ocular features. To reduce processing of the composite image, the image quality assessor may filter a significant number of the frames that do not include one or more ocular features. Further, in one or more embodiments, the image quality assessor reduces processing expense by sampling selected frames having timestamps that are not adjacent in time to each other. At least two of the frames include the same ocular or other anatomical feature, and the composite image manager may form a composite image of the patient's eye by stitching the frames together.

In accordance with embodiments of the present disclosure, the image quality assessor may generate and provide a video quality score of the captured video to the PCP in real time or near real time. For example, the image quality assessor may generate and provide the video quality score to the PCP while the PCP is still meeting with the patient. The PCP may review the video quality score while meeting with the patient and determine whether he or she should capture a new video. This may help to provide the remote specialist with a video that is of diagnosable quality without requiring one or more follow up visits from the patient. In some embodiments, this may help to ensure that the patient receives timely health care advice from the specialist.

As mentioned above, and as will be discussed in further detail herein, the image quality assessor may utilize a filtering process to reduce the number of images (e.g., the number of frames from the video) that it analyzes. For example, the image quality assessor may apply an initial filter to discard from analysis any images that have insufficient luminance, saturation, and/or sharpness values. Such a filter can significantly speed up the analysis process as well as help reduce the overall processing of the captured eye exam. Indeed, by reducing the number of images from the captured video content in this manner, the image quality assessor can significantly reduce expenses of processing resources and, in some cases, reduce the quantity of data transmitted between devices over a network. After discarding all the images that do not have sufficient luminance, saturation, and sharpness values, an ensemble neural net analyzes the remaining images for features relating to the physiological information collected. The ensemble neural net may help to reduce the processing time and expense of computing resources utilized by the image quality assessor, thereby allowing it to provide the image quality score to the PCP faster.

In one or more embodiments described herein, the image quality assessor provides a sequenced approach for filtering frames from the video content. For example, in some embodiments, for an eye exam, an initial neural net may examine the images for images of an eye. An eye exam recording may include images other than images of an eye if the PCP begins recording before the ophthalmoscope is in position in front of the patient's eye. Any images that do not include an eye may be discarded from examination. In some embodiments, the ensemble neural net may analyze the images for eye features, such as the optic nerve, the macula, vasculature, and so forth. The ensemble neural net may include multiple neural nets that are trained to identify such eye features. For example, the ensemble neural net may include a separate neural net that identifies the presence of an eye, a neural net that identifies the presence of the optic nerve, a neural net that identifies the presence of the macula, a neural net that identifies the presence of vasculature, and so forth.

The neural nets may provide an image quality score of the images, depending on how closely features within the image match pre-determined metrics. Using the image quality score of the images, the image quality assessor may provide a video quality score. The video quality score may be representative of whether the eye features are visible in the video, how many frames include the eye features, and/or the clarity of the images. In some embodiments, the video quality score may be sorted into multiple color-coded categories. For example, high video quality scores that likely include all of the eye features may be coded green, medium video quality scores that may not include all of the eye features or may have image clarity issues may be coded yellow, and low video quality scores that do not detect one or more eye features or have serious image clarity issues may be coded red. If the PCP receives a video quality score in the green zone, he or she may immediately send the video to the remote specialist for review. If the PCP receives a video quality score in the yellow zone, he or she may review the video and determine whether he or she should take a new video. If the PCP receives a video quality score in the red zone, he or she may immediately determine that he or she needs to take a new video. The video quality score may help the PCP to make an informed decision about whether the video includes all of the relevant eye features that the remote specialist may use to provide health care advice.

In accordance with embodiments of the present disclosure, the ensemble neural nets may include machine learning models that are trained to identify one or more specific health-related features. For example, a neural net may be trained to identify the optic nerve using images of the interior of eyes that have been reference tagged as including the optic nerve. In some examples, a neural net may be trained to identify the macula using images of the interior of eyes that have been reference tagged as including the macula. In some examples, a neural net may be trained to identify vasculature using images of the interior of eyes that have been reference tagged as including vasculature.

The image quality assessor system provides many advantages and benefits over conventional systems and methods. For example, by utilizing a filtering process and the ensemble neural net the image quality assessor system improves processing speeds relative to conventional systems. Specifically, the image quality assessor improves processing speed by reducing the total number of images that are processed and/or communicated over a network. This not only enables the image quality assessor to significantly reduce the processing and bandwidth expenses of analyzing full-resolution video content, but may also provide the PCP with close to real-time feedback indicating diagnosable quality of the video taken, thereby allowing the PCP to take another video if desired.

In some examples, the image quality assessor may provide the benefit of providing accurate and reliable image quality scores and video quality scores of images using the ensemble neural net. The ensemble neural net may accurately and reliably identify features of the eye. Indeed, the ensemble neural net may identify features of the eye that the PCP is not trained or not experienced to identify. This may help to provide a remote specialist with reliable information in connection with capturing the video content, thereby allowing the remote specialist to review the captured video and provide a medical diagnosis and/or advice based on video content captured by a non-specialized PCP or other individual.

In some embodiments, the image quality assessor may allow a PCP to collect anatomical or physiological information using readily available equipment and materials. For example, the image quality assessor may allow the PCP to use a smartphone connected to an ophthalmoscope to generate a recording of the interior of a patient's eye. The image quality assessor may analyze the captured video and determine whether the video is of a high enough quality for a remote specialist to use to provide advice and/or a diagnosis. Allowing a PCP to use readily available equipment may help to reduce equipment and operating costs for the PCP and improve the likelihood that the user may receive specialist care.

It will be understood that while one or more embodiments described herein relate specifically to capturing video content in connection with an eye exam and determining diagnosable quality of the video content using models trained specifically for detecting optical features, features and functionalities described in connection with the image quality assessor and other components herein may similarly apply to other specialized fields. For example, a mobile device may be tasked with capturing video content related to other fields of medicine while the image quality assessor may include models trained to detect or otherwise identify predetermined features in connection with the other fields of medicine for use by a specialist in the other field(s) of medicine. Accordingly, while examples discussed herein relate primarily to capturing video in connection with eye exams, many features may apply to other medical fields.

As illustrated by the foregoing discussion, the present disclosure utilizes a variety of terms to describe features and advantages of the image quality assessor system. Additional detail is now provided regarding the meaning of such terms. For example, as used herein, the term "PCP" or "primary care provider" refers to a health care provider that provides primary care for a patient. For example, a PCP may provide regular or scheduled physicals or wellness checkups. A PCP may include any person that the patient uses for general health and wellness. Such PCPs include general practice doctors, optometrists, general dentists, and so forth.

As used herein, a "remote" specialist or health care provider may be any health care professional or provider that is not located in the same room as the patient and/or the PCP. For example, a remote specialist may be located in a different office, a different building, a different city, a different county, a different state, a different time zone, a different country, or be otherwise located in a different location from the user. The remote specialist may communicate with the PCP and/or the patient via an internet connection or other wireless connection. The remote specialist may have specialty in a particular area of medicine. For example, a remote specialist may be an ophthalmologist, an ear-nose-throat doctor, an oral surgeon, any other specialist, and combinations thereof.

As used herein, "medical advice," "health care advice," "diagnosis," and other similar terms may be any information provided to a patient to maintain or improve his or her health. Such advice may include a diagnosis of a disease, ailment, condition, or other diagnosis. In some embodiments, such advice may include providing a prescription for medicine. In some embodiments, such advice may include providing a therapy procedure.

As used herein, an "image quality score" may be a score or value assigned to a frame or image of a video taken by a PCP. The image quality score may be based on one or more metrics. For example, the image quality score may be based on one or more of image clarity, the presence of an anatomical feature in the image, and so forth. The image quality score may be a composite score, a weighted average, or any other type of score. In some embodiments, the image quality score may be a numerical value, such as a value from 0 to 10, with 10 being a perfectly clear image that includes the target anatomical features, and 0 being a low clarity image and/or that does not include any target anatomical features. In some embodiments, the image quality score may be a classification of video content indicating whether the video content is above or below an acceptable threshold or whether there is uncertainty associated with the video content. In one or more embodiments described herein, the image quality score refers to a classification of color for quick and easy reference.

As used herein, a "video quality score" may be a score or value assigned to an entire captured video taken by a PCP. The video quality score may be based on the image quality scores of the individual frames of the video. In some embodiments, the video quality score may be an average or a weighted average of the image quality scores. In some embodiments, the video quality score may be based on how many of the frames have an image quality score above a particular threshold. In some embodiments, the video quality score may be based on how many of the frames include a particular anatomical feature. In some embodiments, the video quality score may be a numerical value, such as a value from 0 to 10, with 10 being a video that includes the target anatomical features in high clarity, and 0 being a low clarity video and/or that does not include any target anatomical features. In some embodiments, the video quality score may be a letter value, such as A, B, C, D, E, F, and so forth. In some embodiments, the video quality score may be color coded for quick and easy reference.

As used herein, the term "real time" may be any response time for a video analysis that is responsive to allow for a decision to be made based on the video analysis within a single meeting or event. For example, a PCP that prepares an eye exam video and submits it to an image quality assessor may receive a response in real time if he or she receives a response while still attending the patient. In some embodiments, the PCP may receive a response in real time if he or she receives a response while discussing the video collection with the patient. In some embodiments, real time may be any response time that is less than 30 s, less than 20 s, less than 15 s, less than 10 s, less than 5 s, less than 4 s, less than 3 s, less than 2 s, less than 1 s, less than 0.5 s, less than 0.1 s, or any value therebetween.

Embodiments of the present disclosure may be described with reference to eyes, an eye exam video, ocular features (e.g., optic nerve, macula, vasculature), optometrist, ophthalmologists, and other eye health related entities, diagnoses, and advice. However, as noted above, it should be understood that embodiments of the present disclosure may be applied to any anatomical feature or medical specialization. For example, embodiments of the present disclosure may be applied to the mouth, teeth, the ear, skin, bones, any other anatomical feature, and combinations thereof.

FIG. 1 is a representation of a remote health system 100, according to at least one embodiment of the present disclosure. A PCP may utilize a mobile device 102 to record or capture a video of an anatomical feature or to record physiological information of a user. The PCP may record the video using a hand-held mobile device 102, such as a smartphone, tablet, or other readily accessible hand-held mobile device 102.

The mobile device 102 may transmit the video to a cloud server 106. The cloud server 106 may include an image quality assessor 108. As will be discussed in further detail herein, the image quality assessor 108 may perform an image quality assessment on the captured video 104-1. The image quality assessor 108 may generate a video quality score 110 of the video 104-1. The image quality assessor 108 may provide the video quality score 110 to the mobile device 102. The PCP may then review the video quality score 110 to determine whether he or she should transmit a copy of the video 104-2 to a remote specialist device (or simply, "remote specialist 112").

In accordance with embodiments of the present disclosure, the image quality assessor 108 may review the video 104-1 in real time and provide the PCP with the video quality score 110 in real time. Put another way, reviewing the video and providing the PCP with the video quality score 110 occurs in real time. The PCP may then review the video quality score 110 and determine whether he or she should record an additional video. In some embodiments, the video quality score may include a value between 0 and 10, with a color coded ranking having scores of 7-10 being green, 4-6.9 being yellow, and scores less than 4 being red. A green ranking may indicate that the PCP may submit a copy of the video 104-2 to the remote specialist 112 without review. A yellow ranking may indicate that the PCP should review the video 104-1 before submitting to the remote specialist 112. A green ranking may indicate that the PCP should record a new video to submit to the remote specialist 112. In some embodiments, the PCP may review each of the videos, regardless of the ranking, before sending to the remote specialist.

In some embodiments, the image quality assessor 108 may provide an indication to the mobile device 102 regarding whether the captured video is suitable for use in a remote medical evaluation. For example, the indication may include the video quality score 110. In some examples, the indication may include a color coding of the video quality score 110. In some examples, the indication may include one or more deficiencies of the video 104-1. For example, the video quality score 110 may include an indication that the image quality assessor 108 did not detect a particular anatomical feature. The PCP may use this indication during his or her review to determine whether he or she should record a new video.

After approval of the video 104-1, the PCP may transmit the video 104-1 to the remote specialist. In some embodiments, the PCP may send an indication to the cloud server 106 that the video is approved, and to transmit a copy of the video 104-2 to the remote specialist 112. In some embodiments, the PCP may have a list of remote specialists 112 on the mobile device 102. He or she may select a desired remote specialist 112, and provide the cloud server 106 with an indication that the video is approved and the selected remote specialist 112. The cloud server 106 may then transmit the copy of the video 104-1 to the remote specialist 112. In some embodiments, the mobile device 102 may transmit the copy of the video 104-2 to the remote specialist 112 directly.

In one or more embodiments, the copy of the video 104-2 refers to a full copy of the video 104-1 provided for analysis by the image quality assessor 108. Alternatively, in one or more embodiments, the copy of the video 104-2 refers to a partial copy including only a subset of video frames from the captured video 104-1. For example, as will be discussed in further detail herein, the image quality assessor 108 may selectively identify video frames that include particular features and/or satisfy a threshold of image clarify. In one or more embodiments, the image quality assessor 108 may provide the subset of video frames rather than a full copy of the video in an effort to save time and network resources for the cloud 106 and/or remote specialist 112. In one or more embodiments, the image quality assessor 108 posts both a full copy of the video 104-2 as well as select portions.

In some embodiments, the video 104-1 may be deleted from the mobile device 102. For example, after the PCP approves the video 104-1 and submits a copy to the remote specialist 112, the cloud server 106 may send an instruction to the mobile device 102 to delete the video 104-1 from the local memory. In some embodiments, the memory on the mobile device 102 may be deleted periodically, such as hourly, daily, weekly, and so forth. This may help to maintain patient privacy. In some embodiments, this may help to maintain a working memory on the mobile device 102 that would otherwise become clogged with videos of the many patients that visit the PCP.

In some embodiments, the image quality assessor 108 may select one or more thumbnails, or frames from the video 104-1, for the mobile device 102 to store in the patient's profile to indicate that a video was taken. In some embodiments, the mobile device 102 may store the video quality score 110 of the video 104-1 on the mobile device 102 to allow the PCP to have a record of the recording of the video 104-1 and the video quality score 110. In some embodiments, upon request from the PCP, the cloud server 106 may send the video 104-1 back to the mobile device 102 for review by the PCP, if desired.

When the remote specialist 112 receives the copy of the video 104-2, he or she may analyze the video content. The remote specialist 112 may then prepare medical advice and/or a diagnosis based on the video content. He or she may send the medical advice back to PCP via the cloud server 106. The PCP may then provide the patient with the medical advice and/or diagnosis. As discussed herein, this may help to improve patient access to the remote specialist 112.

Figure 2:
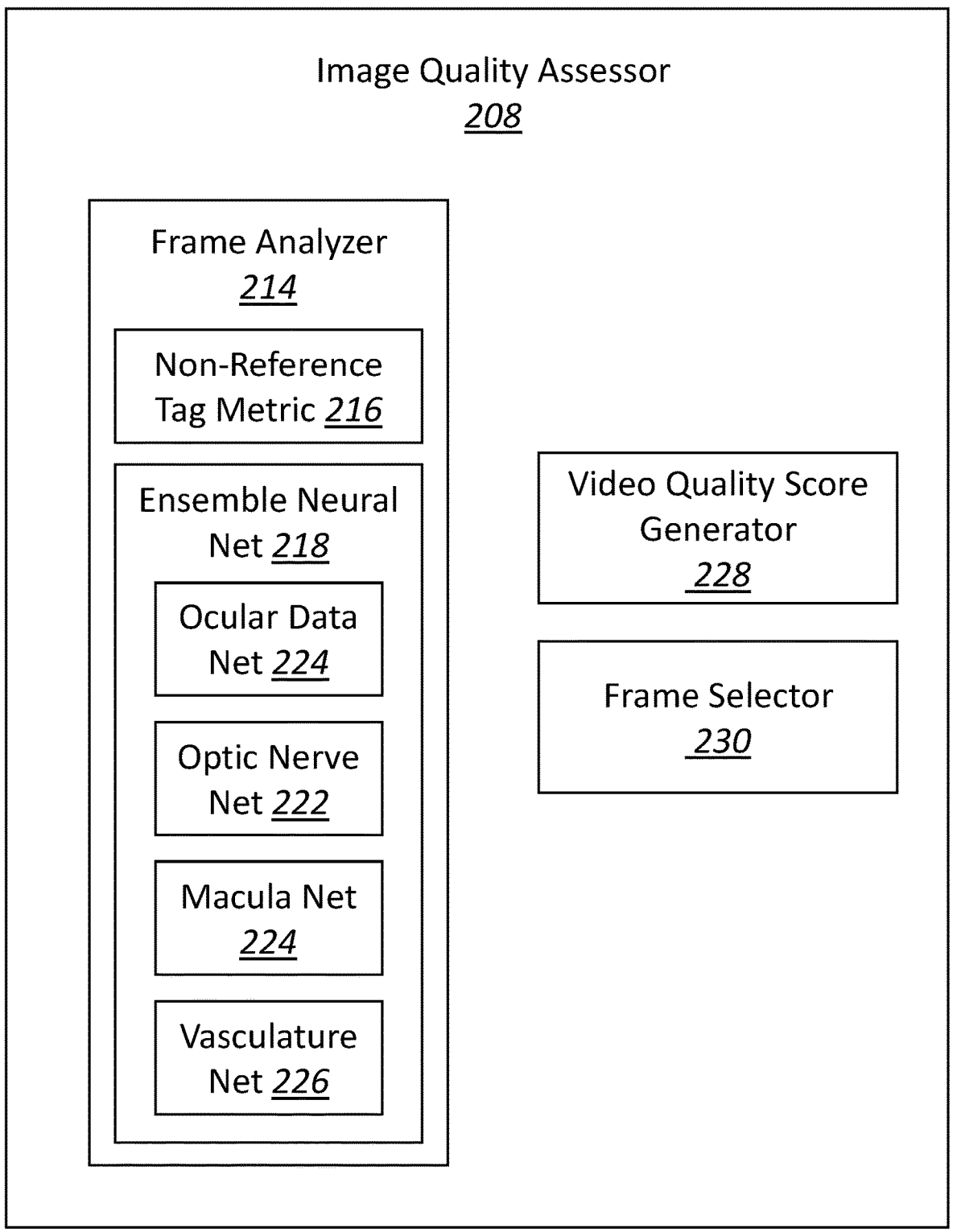
FIG. 2 illustrates a block diagram of an image quality assessor in accordance with one or more embodiments.

FIG. 2 is a representation of an image quality assessor 208, according to at least one embodiment of the present disclosure. The image quality assessor 208 may include a frame analyzer 214. As discussed in further detail herein, when the image quality assessor 208 receives the video from the mobile device, the frame analyzer 214 may analyze the individual frames of the video. The frame analyzer 214 may generate one or more image quality scores for the individual frames of the video.

In accordance with embodiments of the present disclosure, the frame analyzer 214 may compare the individual frames to one or more predetermined metrics. For example, the frame analyzer 214 may compare the frames using non-reference tagged metrics 216. Non-reference tagged metrics may be metrics that relate to the clarity of the images, including luminance, saturation, sharpness, blurriness, color balance, any other clarity metric, and combinations thereof. As discussed herein, the frame analyzer 214 may perform an initial analysis of the frames using the non-reference tagged metrics 216 and filter out or discard any images that do not pass a particular threshold. This analysis may be computationally fast, and may reduce the number of images that are analyzed by other components of the frame analyzer 214.

The frame analyzer 214 may further include an ensemble neural net 218. The ensemble neural net 218 may analyze the frames of the video for one or particular features or structures in the images. For example, for an eye exam video, the ensemble neural net 218 may analyze the frames for different ocular features, such as the optic nerve, the macula, and/or vasculature. In some embodiments, the ensemble neural net 218 may include a plurality of neural nets working in concert. For example, the ensemble neural net 218 may include an ocular data net 220, an optic nerve net 222, a macula net 224, and a vasculature net 226. Furthermore, it should be understood that the ensemble neural net 218 may include any other type of net related to any other desired feature of the images of the video.

Each of the nets in the ensemble neural net 218 may be directed to different elements of the images captured in the video. For example, the ocular data net 220 may be directed to identifying whether the frame includes ocular data or other, unrelated data. The optic nerve net 222 may be directed to identifying whether the frame includes an image of the optic nerve. The macula net 224 may be directed to identifying whether the frame includes an image of the macula. The vasculature net 226 may be directed to identifying whether the frame includes an image of the vasculature. Utilizing the ensemble neural net 218 may allow for fast and reliable identification of the ocular features in the video.

In some embodiments, the nets of the ensemble neural net 218 may be applied to the video sequentially. If a particular net does not identify its subject matter in the image, the image may be discarded from the analysis, and the subsequent neural nets may not analyze that image. This may help to improve the processing speed of the frame analyzer 214. For example, the ocular data net 220 may analyze the individual frames to determine whether they include images of an eye. If they do not include images of an eye, then the optic nerve net 222, the macula net 224, and the vasculature net 226 will not identify their respective features. By discarding frames that do not include images of an eye before they are sent to the other nets, the frame analyzer 214 may reduce the total processing of the video, thereby reducing the overall processing time. As discussed herein, and in combination with discarding images based on the non-reference tagged metrics, this may reduce the total processing time of the video by a factor of three. In some embodiments, this may reduce the total processing time of the video by a factor of ten or more. In this manner, the frame analyzer 214 may help the image quality assessor 208 to generate a video quality score in real time while significantly reducing the expense of computing resources (e.g., cloud computing resources).

In some embodiments, two or more nets of the ensemble neural net 218 may be applied to the video simultaneously or at the same time. In this manner, the frame analyzer 214 may quickly and accurately identify the presence of different ocular features in different frames of the video. For example, a video having a high video quality score may not have the optic nerve imaged in every frame. By analyzing the images for particular ocular features simultaneously, then the frame analyzer 214 may determine whether the video as a whole includes one or more frames including the identified ocular features. In some embodiments, the neural nets of the ensemble neural nets 218 may be applied sequentially, but one or more nets may not discard an image if it does not include the identified ocular feature, thereby allowing subsequent neural nets to identify their identified ocular feature.

In some embodiments, the frame analyzer 214 may prepare an image quality score for each frame of the video. For example, using the comparison to the predetermined metrics, the frame analyzer 214 may prepare an image quality score that incorporates image clarity and the presence of one or more ocular features. In some embodiments, the image quality score may include a representation of how closely a feature in the frame matches an ocular feature. For example, the optic nerve net 222 may provide an indication of how closely a feature in the frame matches an optic nerve. The image quality score may be at least partially based on this closeness. In some embodiments, the image quality score may be a numerical score, such as a score from 0 to 10.

In some embodiments, the image quality score may include information in addition to or as an alternative to a numerical score. For example, the image quality score may include an indication of the presence or lack of presence of a particular ocular feature, an indication of the clarity of the image, and so forth. In some embodiments, the image quality scores may be attached to the metadata for each individual frame. In some embodiments, the image quality scores may be attached to the metadata for the video with a listing of the scores and associated information for each frame. In some embodiments, the frame analyzer 214 may prepare a feature-specific image quality score for each analyzed feature. For example, a single frame may have an optic nerve image quality score based on the presence of the optic nerve, a macula image quality score based on the presence of the macula, a vasculature image quality score based on the presence of vasculature, a clarity image quality score based on the clarity of the image, and so forth.

While one or more embodiments described herein refer specifically to examples where the non-reference tag metric 216 and the ensemble neural net 218 are analyzed on the same device or system of devices and inclusive within the image quality assessor 208, other implementations may include portions of the frame analyzer 214 implemented across different devices. For example, in one or more embodiments, the frame analyzer 214 includes a first model trained to analyze the non-reference tag metric(s) 216 and a second model(s) including the ensemble neural net 218 on different devices. Indeed, in one or more embodiments, a first portion of the frame analyzer 214 may be implemented on the mobile device to provide an initial analysis for image clarity prior to providing the video content for further analysis using a second portion of the frame analyzer 214 configured to apply the ensemble neural net 218 for further analysis. This may improve the analysis system (e.g., system 100) by decreasing the quantity of data transmitted over a wireless network by way of filtering out images that are below a threshold level of image clarity or simply preventing transmission of video content that would ultimately be rejected by the image quality assessor 208.

In some embodiments, the image quality assessor may include a video quality score generator 228. The video quality score generator 228 may utilize the information from the frame analyzer 214 to generate a video quality score to send to the PCP. For example, the video quality score generator 228 may generate the video quality score based the image quality scores of the individual frames of the video. For example, the video quality score may include an average or a weighted average of all of the image quality scores of the frames of the video.

In some embodiments, the video quality score generator may generate the video quality score based on the overall presence or lack of presence of individual ocular features. For example, a video may include many frames having a high image quality score based on the presence of the optic nerve, but few or no frames that include the macula. In some embodiments, the video quality score generator may utilize feature-specific image quality scores to generate the video quality score. In this manner, the video quality score may be inclusive of all of the analyzed features.

In some embodiments, the video quality score generator may generate a video quality report to send to the PCP. The video quality report may include an analysis of which ocular features were detected or not detected in the video. For example, the video quality report may include an indication that a particular ocular feature was not detected in the video. The PCP may use the video quality report in combination with the video quality score to determine whether he or she should capture a new video.

In some embodiments, and as will be discussed in further detail herein, the image quality assessor 208 may include a frame selector 230. Using the image quality scores developed by the frame analyzer 214, the frame selector 230 may identify or select one or more representative frames from the video. In some embodiments, the representative frames may be transmitted to the mobile device to be used as a thumbnail for the video on the patient's profile. In some embodiments, the representative frames may be identified and their locations marked on the video to transmit to the remote specialist. The remote specialist may then be able to review the representative frames in conjunction with the video to provide medical advice and/or a diagnosis to the user.

Each of the components of the image quality assessor 208 can include software, hardware, or both. For example, the components can include one or more instructions stored on a computer-readable storage medium and executable by processors of one or more computing devices, such as a client device or server device. When executed by the one or more processors, the computer-executable instructions of the image quality assessor 208 can cause the computing device(s) to perform the methods described herein. Alternatively, the components can include hardware, such as a special-purpose processing device to perform a certain function or group of functions. Alternatively, the components of the image quality assessor 208 can include a combination of computer-executable instructions and hardware.

Furthermore, the components of the image quality assessor 208 may, for example, be implemented as one or more operating systems, as one or more stand-alone applications, as one or more modules of an application, as one or more plug-ins, as one or more library functions or functions that may be called by other applications, and/or as a cloud-computing model. Thus, the components may be implemented as a stand-alone application, such as a desktop or mobile application. Furthermore, the components may be implemented as one or more web-based applications hosted on a remote server. The components may also be implemented in a suite of mobile device applications or "apps."

Figure 3:
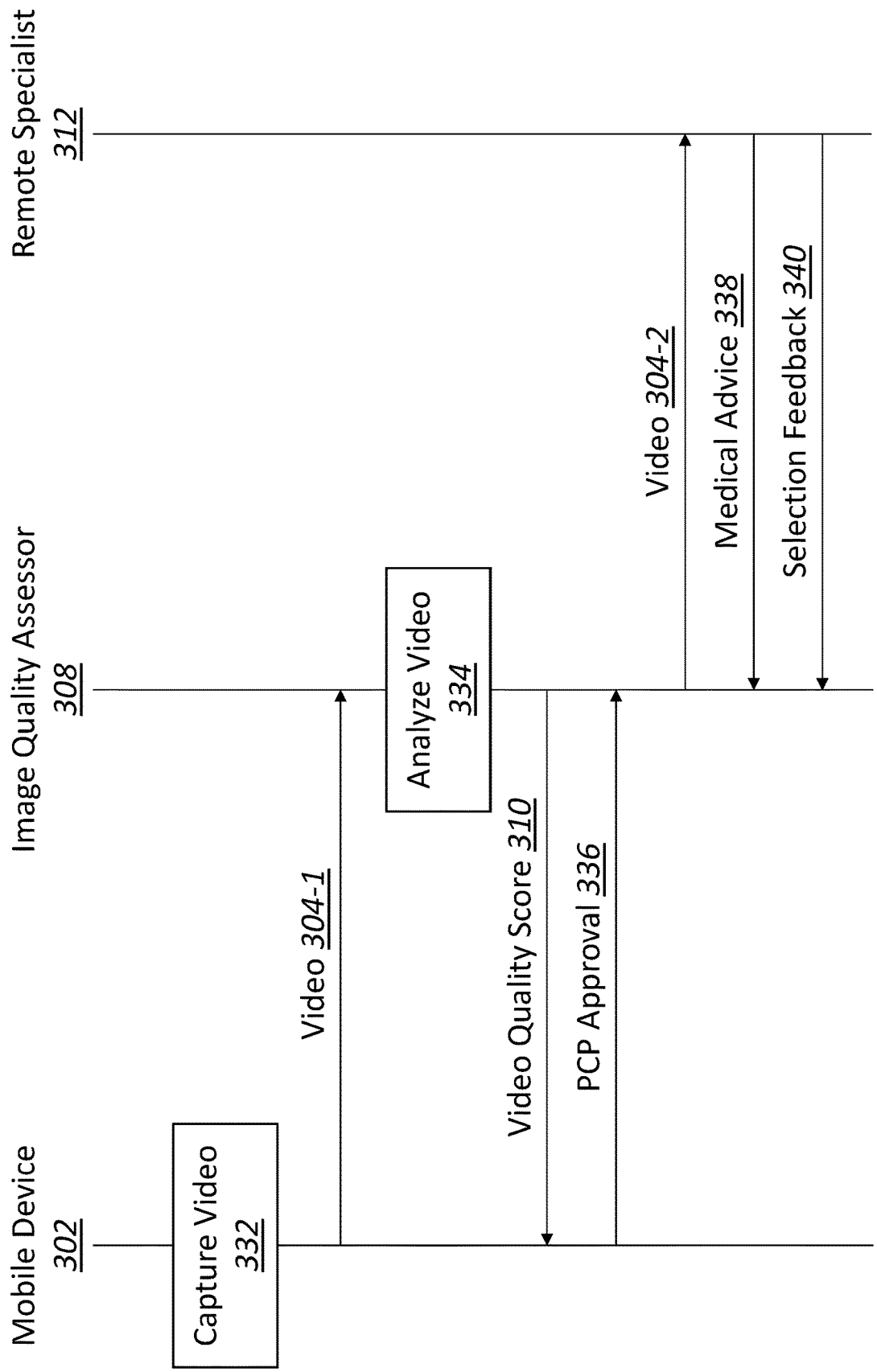
FIG. 3 illustrates a chart of a remote healthcare system in accordance with one or more embodiments.

FIG. 3 is a chart of a remote health system 300, according to at least one embodiment of the present disclosure. In the remote health system 300, a PCP may capture 332 a video 304 on a mobile device 302. The mobile device 302 may transmit the video to an image quality assessor 308 on a cloud server. The image quality assessor may analyze 334 the video 304 and prepare a video quality score 310 of the video 304. The image quality assessor 308 may transmit the video quality score 310 to the mobile device 302. As discussed herein, the image quality assessor 308 may transmit the video in real time.

The PCP may review the video quality score 310 at the mobile device and determine whether the video 304 is of a diagnosable quality. In some embodiments, the PCP may determine that he or she should capture 332 a new video 304, and may transmit the new video to the image quality assessor 308, which may analyze 334 the video and prepare and send a new video quality score 310 to the mobile device 302. This process may be repeated until the PCP sends his or her approval 336 back to the image quality assessor 308.

When the image quality assessor 308 receives the approval 336 from the PCP, then the image quality assessor 308 may transmit the video 304 to the remote specialist 312. The remote specialist 312 may review the video and provide medical advice 338 for the patient. In some embodiments, the remote specialist 312 may transmit the medical advice 338 to the image quality assessor 308, and the image quality assessor 308 may disseminate the medical advice 338 to the patient. For example, the image quality assessor 308 may transmit the medical advice to the mobile device 302 so the PCP can provide the medical advice 338 to the patient. In some embodiments, the remote specialist 312 may transmit the medical advice 338 directly to the patient.

In some embodiments, the remote specialist 312 may provide selection feedback 340 to the image quality assessor 308. The selection feedback 340 may include feedback regarding the video quality score 310, any selected frames, and whether the ensemble neural net properly identified the anatomical features of interest in the video 304. The image quality assessor 308 may incorporate the selection feedback 340 to more accurately and reliably identify the anatomical features.

Figure 4:
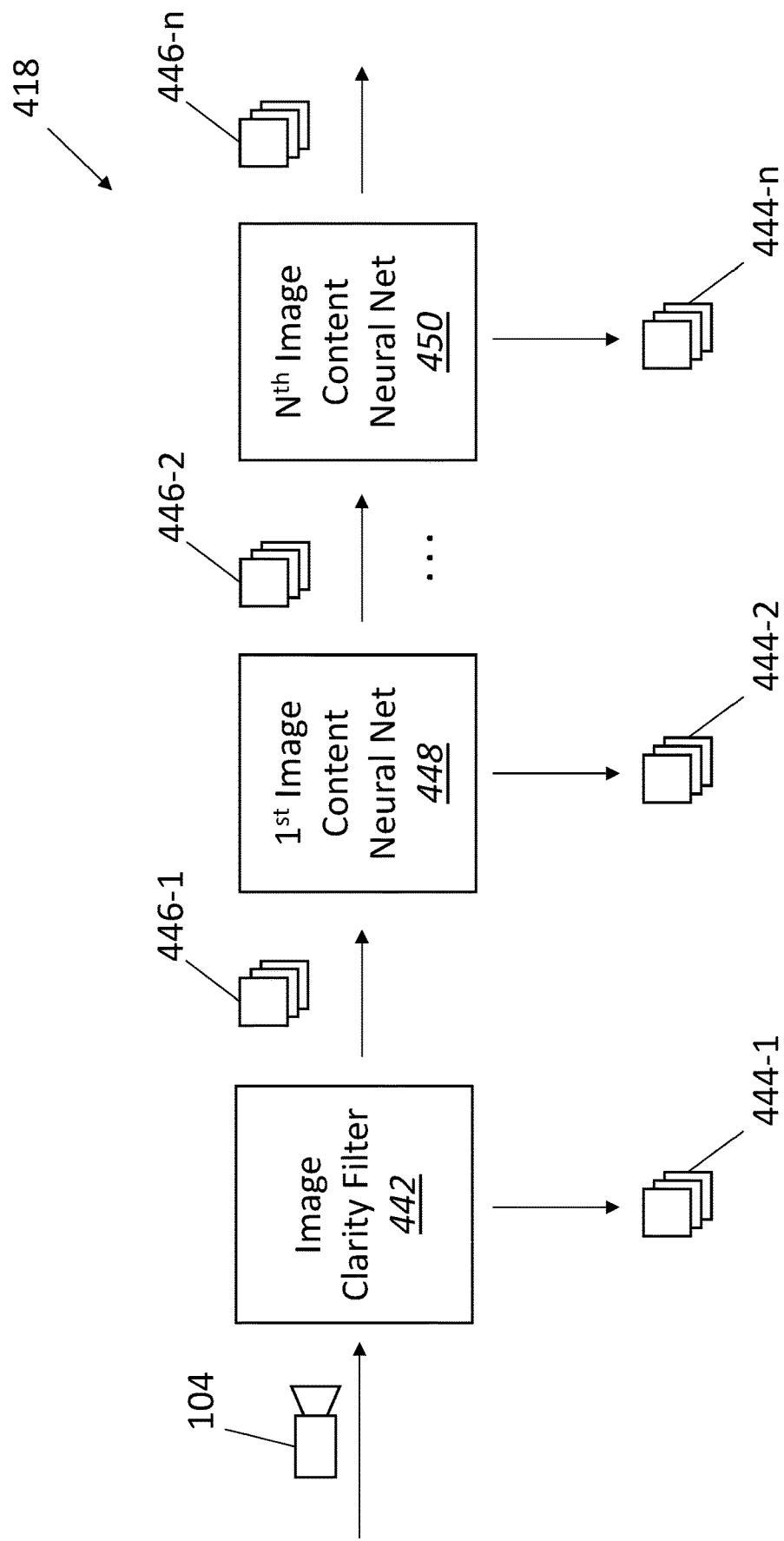
FIG. 4 illustrates a diagram of an ensemble neural net in accordance with one or more embodiments.

FIG. 4 is a representation of an ensemble neural net 418, according to at least one embodiment of the present disclosure. The ensemble neural net 418 may receive a video from a mobile device. In the embodiment shown, the ensemble neural net 418 may first review the video for non-reference tagged metrics. For example, the ensemble neural net 418 may pass the video through an image clarity filter 442. The image clarity filter 442 may review each individual frame from the video for image quality metrics, such as luminance, saturation, sharpness, and so forth. Any frame whose image does not pass a minimum threshold for image clarity may be discarded from the analysis. This may reduce the total number of frames that may be reviewed by subsequent portions of the ensemble neural net. While the image clarity filter 442 may not use a neural net to review the frames of the video, for ease of illustration and discussion, the image clarity filter 442 has been included in the discussion of the ensemble neural net 418. However, it should be understood that any filtering mechanism may be used to analyze the frames of the video 404 and discarded images 444-1 that do not meet the threshold image clarity value.

In some embodiments, a first set of passing frames 446-1 (e.g., the frames whose images are above the threshold for image clarity) may be reviewed by a first image content neural net 448. The first image content neural net 448 may review the passing frames 446-1 for a first content, and discard frames 444-2 that do not include the first content and pass frames 446-2 that do include the first content. For example, the first content may be whether the frame includes an image of an eye. The first image content neural net 448 may discard frames 444-2 that do not include an image of an eye, and pass frames 446-2 that do include an image of an eye. This may further reduce the total number of frames that are analyzed by subsequent neural nets. In this manner, the total processing time and resources of the ensemble neural net 418 may be reduced.

The passing frames 446-2 may be further reviewed by n number of neural nets, where n corresponds to the number of neural nets used to identify additional features in the frames. As discussed herein, in some embodiments, the nth neural net 450 may include a plurality of neural nets that are applied to the passing frames 446-2 in tandem or simultaneously. In some embodiments, the nth neural net 450 may discard frames 444-*n* that do not include the identified feature and pass frames 446-*n* that do include the identified feature.

In some embodiments, each neural net may prepare an image quality score for each of the individual frames analyzed. The image quality score may be attached to each individual frame as metadata and include how closely the image in the frame matches the neural net's particular feature. In some embodiments, the ensemble neural net may send discarded frames 444 and the passing frames 446 to a video quality score generator to prepare a video quality score of the video.

Figure 5:
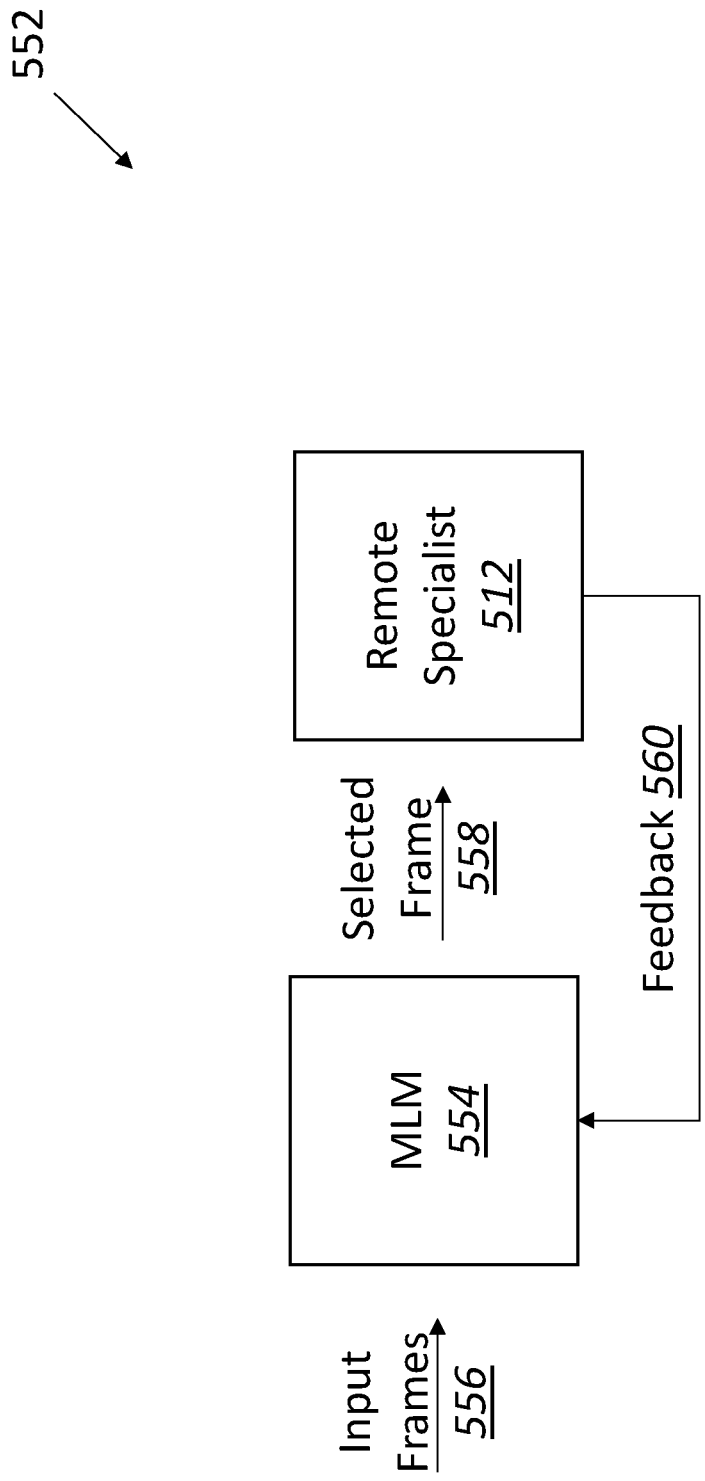
FIG. 5 illustrates a diagram of a machine learning system in accordance with one or more embodiments.

FIG. 5 is a representation of a machine learning system 552, according to at least one embodiment of the present disclosure. In accordance with embodiments of the present disclosure, the machine learning system 552 may be used in one or more neural nets, as discussed herein. For example, the machine learning system 552 may be used to identify images in frames from a video that include a particular anatomical feature.

The machine learning system 552 may include a machine learning model (MLM) 554. The MLM 554 may be trained to identify anatomical features. For example, the MLM 554 may be trained using a library of images that are reference tagged with the anatomical feature of interest. For example, the MLM 554 may be trained to identify the presence of the optic nerve. The MLM 554 may be trained using a library of images that include reference tags for an optic nerve. Using the library of images, the MLM 554 may identify the features in an image that correspond to an optic nerve.

Humans have a large amount of variance between people in the structure of an optic nerve. For example, an optic nerve may be damaged, diseased, of different sizes, and so forth. The image library used to train the MLM 554 may include a large variety of optic nerves, including those that are damaged, diseased, having variable sizes, and so forth. This may help to train the MLM 554 to recognize a variety of optic nerves, thereby helping to identify even diseased or abnormal optic nerves.

In accordance with embodiments of the present disclosure, the MLM 554 may receive one or more input frames 556. The input frames 556 may be individual frames from a video captured by the PCP. For example, the input frames 556 may include the entire video captured by the PCP. In some examples, the input frames 556 may include passing frames from the ensemble neural net.

The MLM 554 may analyze each of the input frames 556 for the presence of the anatomical feature, such as the optic nerve. The MLM may prepare a match value for the input frames 556, which may be a percent match of the image in the input frame 556 with the anatomical feature. In some embodiments, the match value may be used to generate an image quality score of the input frame 556. In some embodiments, the match value may be used to determine whether the anatomical feature is present in the frame. In some embodiments, a threshold match value may be used to determine whether the anatomical feature is present in the frame. For example, an input frame 556 having match value greater than the threshold may indicate that the anatomical feature was detected in the input frame 556, while an input frame 556 having a match value less than the threshold may indicate that the anatomical feature was not detected in the input frame 556. In some embodiments, the match value may be set low to help ensure that variations in anatomical features across different patients are accounted for.

In some embodiments, using the match values, the MLM 554 may output one or more selected frames 558. The selected frames 558 may be frames that the MLM 554 has identified include the specified anatomical feature. The selected frames 558 may be transmitted to a remote specialist 512. The remote specialist may analyze the selected frames 558 and determine whether thy include the specified anatomical feature. In some embodiments, the selected frames 558 may be used as feedback 560 for the MLM 554. The MLM 554 may be refined using the feedback 560. The refined MLM 554 may then analyze additional input frames 556 for the specified anatomical features. In some embodiments, the refined MLM 554 may more accurately or more reliably detect the anatomical features.

In some embodiments, the MLM 554 may be refined using the feedback 560 on a periodic basis. For example, the MLM 554 may be refined daily, weekly, monthly, yearly, or continuously based on feedback received from remote specialists and/or PCPs. Periodic updating of the MLM 554 may reduce the interruption to the operation of the MLM 554 during operation. In some embodiments, the MLM 554 may be refined on an episodic basis. For example, the MLM 554 may be refined after a certain amount of feedback 560 has been received, after a remote specialist 512 notices a recurring over or under inclusion, or after any other episodic event.

Figure 6:
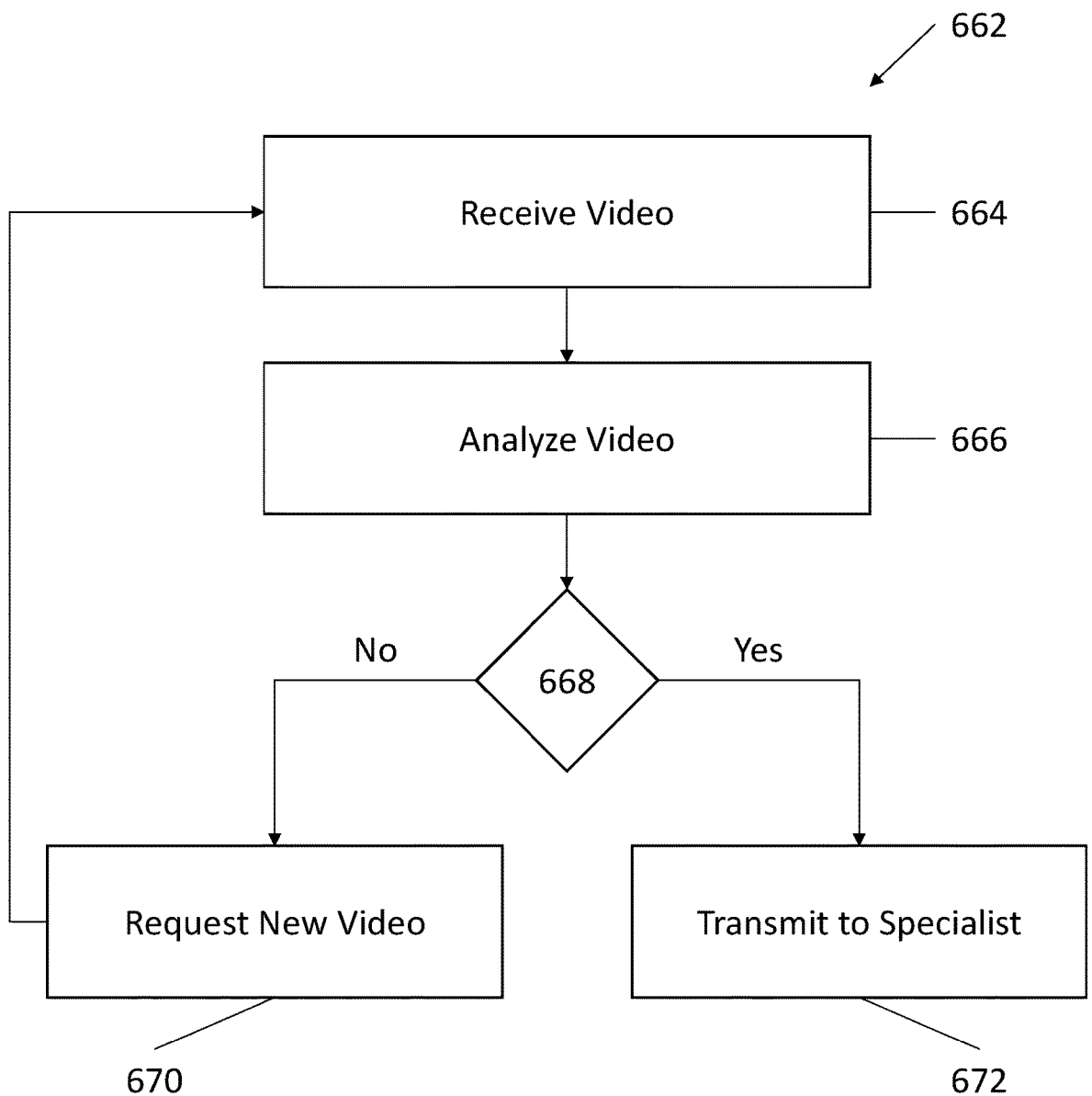
FIG. 6 illustrates a flowchart of a method for providing remote healthcare in accordance with one or more embodiments.
Figure 7:
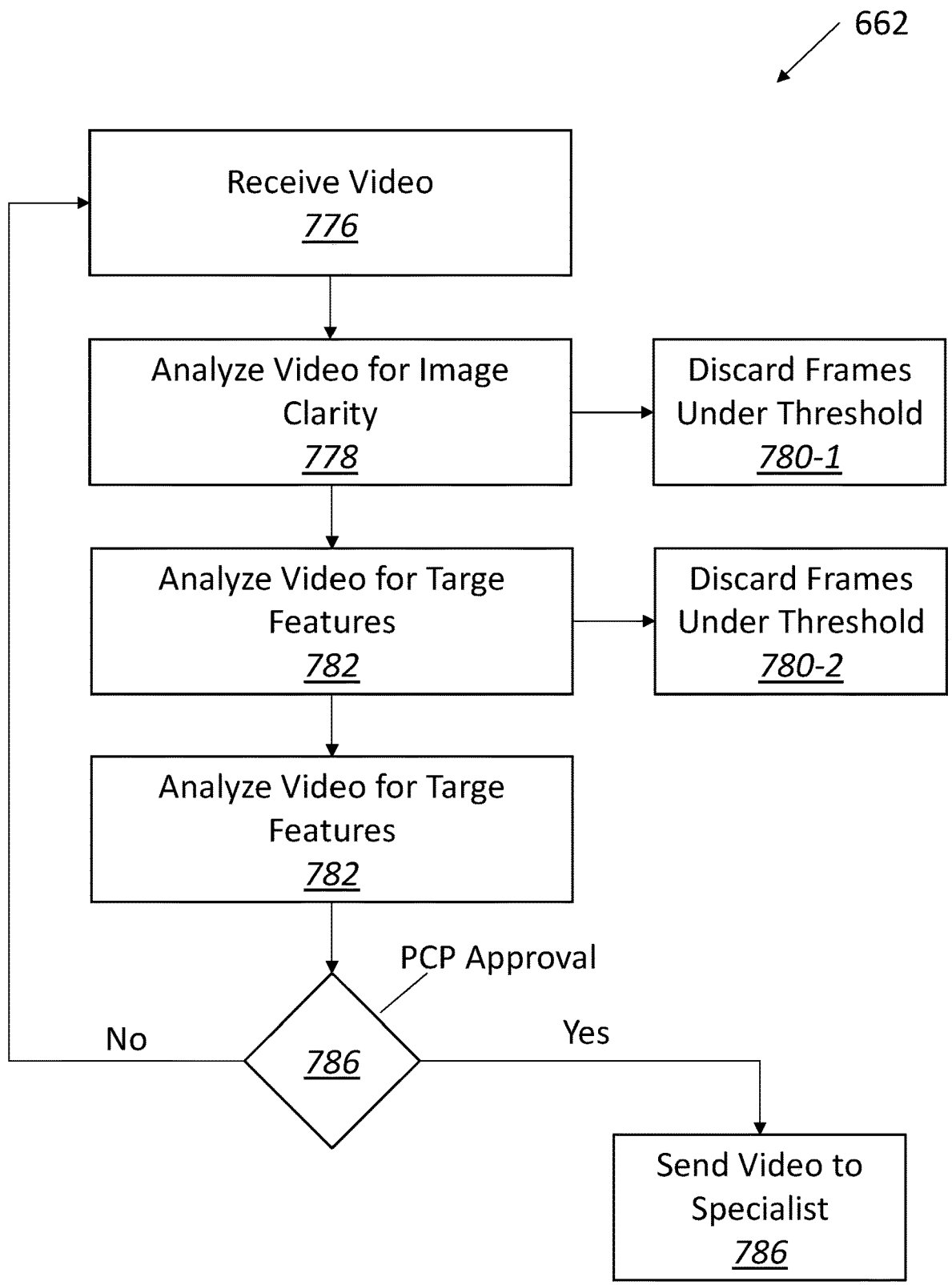
FIG. 7 illustrates a flowchart of a method for providing remote healthcare in accordance with one or more embodiments.
Figure 8:
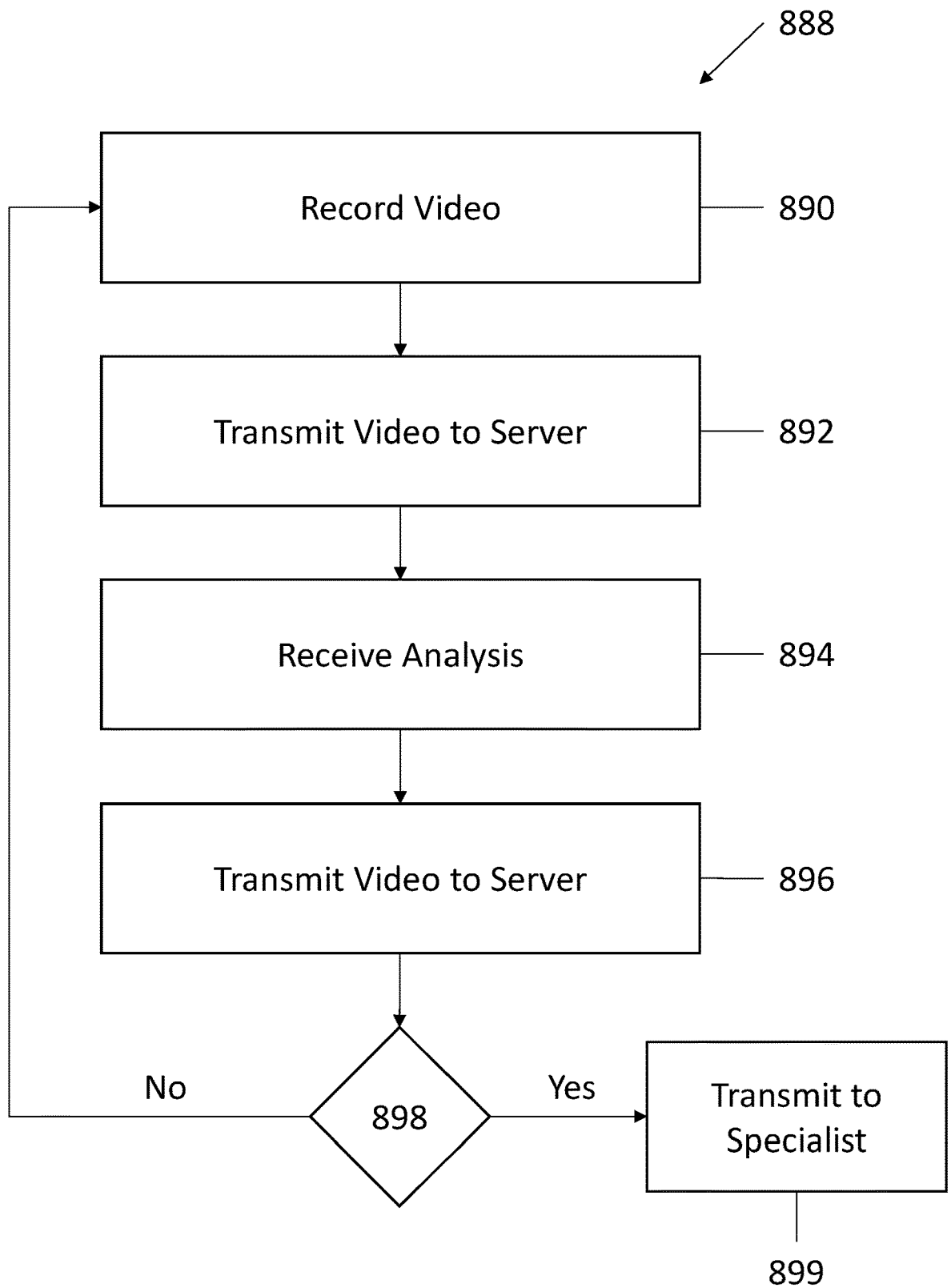
FIG. 8 illustrates a flowchart of a method for providing remote healthcare in accordance with one or more embodiments.

FIGS. 6-8, the corresponding text, and the examples provide a number of different methods, systems, devices, and non-transitory computer-readable media of the remote health system 100. In addition to the foregoing, one or more embodiments can also be described in terms of flowcharts comprising acts for accomplishing a particular result, as shown in FIG. 6-8. FIG. 6-8 may be performed with more or fewer acts. Further, the acts may be performed in differing orders. Additionally, the acts described herein may be repeated or performed in parallel with one another or parallel with different instances of the same or similar acts.

As mentioned, FIGS. 6-8 illustrates a flowchart of a series of acts for providing remote healthcare in accordance with one or more embodiments. While FIGS. 6-8 illustrates acts according to one embodiment, alternative embodiments may omit, add to, reorder, and/or modify any of the acts shown in FIGS. 6-8. The acts of FIGS. 6-8 can be performed as part of a method. Alternatively, a non-transitory computer-readable medium can comprise instructions that, when executed by one or more processors, cause a computing device to perform the acts of FIGS. 6-8. In some embodiments, a system can perform the acts of FIGS. 6-8.

In particular, FIG. 6 is a flowchart of a method 662 for providing remote healthcare, according to at least one embodiment of the present disclosure. The method 662 may be performed by the image quality assessor 208 of FIG. 2. Put another way, the image quality assessor 208 of FIG. 2 may perform at least part of the method 662.

The method 662 may include receiving a video captured from a mobile device at 664. The captured video may be a video that includes physiological information, such as an eye exam video or other video that includes anatomical features of a patient. The method 662 may include analyzing the video for the presence of one or more anatomical features at 666. For example, the image quality assessor may analyze the video for the presence of the optic nerve, the macula, and/or vasculature of the patient.

The method 662 may include determining if the video is of diagnosable quality at 668. As discussed herein, a video may be of diagnosable quality if a remote specialist is able to review the video and provide medical advice and/or a diagnosis based on the video and without personally examining the patient in person. If the video is not of diagnosable quality, then the image quality assessor may request a new video at 670. Based on the request for the new video, the PCP may prepare a new vide and the image quality assessor may receive the new video at 664. This process may be repeated until the video is of diagnosable quality. If the video is of diagnosable quality, then the image quality assessor may transmit the video to the remote specialist at 672.

FIG. 7 is a flowchart of a method 774 for providing remote healthcare, according to at least one embodiment of the present disclosure. The method 774 may be performed by the image quality assessor 208 of FIG. 2. Put another way, the image quality assessor 208 of FIG. 2 may perform at least part of the method 774.

The method 774 may include receiving a video captured by a PCP using a mobile device at 778. The image quality assessor may analyze the video for image clarity at 778. In some embodiments, the image quality assessor may analyze each frame of the video individually for image clarity, including image clarity features such as luminance, saturation, sharpness, and so forth. Any frames that are below a clarity threshold may be discarded at 780-1.

The passing frames (e.g., the frames not discarded, the frames having a clarity that is above the clarity threshold) may then be analyzed for one or more target anatomical features, such as the presence of an optic nerve, macula, or vasculature in an eye exam video, at 782. The image quality assessor may discard any frames that are below a match value threshold at 780-2. In some embodiments, as discussed herein, the image quality assessor may analyze the video for target anatomical features using an ensemble neural network.

In some embodiments, the image quality assessor may use the passing images to prepare a video quality score at 784. The video quality score may be sent to the PCP for review at 786. Upon review, if the PCP does not approve the video, then he or she may record a new video and transmit it to the image quality assessor. The method 774 may then be repeated until the PCP does approve the video. When the PCP approves the video, the video may be sent to the remote specialist at 786.

FIG. 8 is a flowchart of a method 888 for providing remote healthcare, according to at least one embodiment of the present disclosure. In some embodiments, the method 888 may be performed by a mobile device operated by the PCP. Using the mobile device, the PCP may record an examination video at 890. The PCP may transmit the captured video to a remote server at 892. As discussed herein, the remote server may analyze the captured video using an image quality assessor. The remote server may transmit the analysis to the PCP, and the mobile device may receive the analysis at 894. The PCP may review the analysis at 896. If the PCP does not approve 898 the video, then the PCP may record a new video at 890. If the PCP does approve the video, then the PCP may transmit the video to a selected remote specialist at 899.

Figure 9:
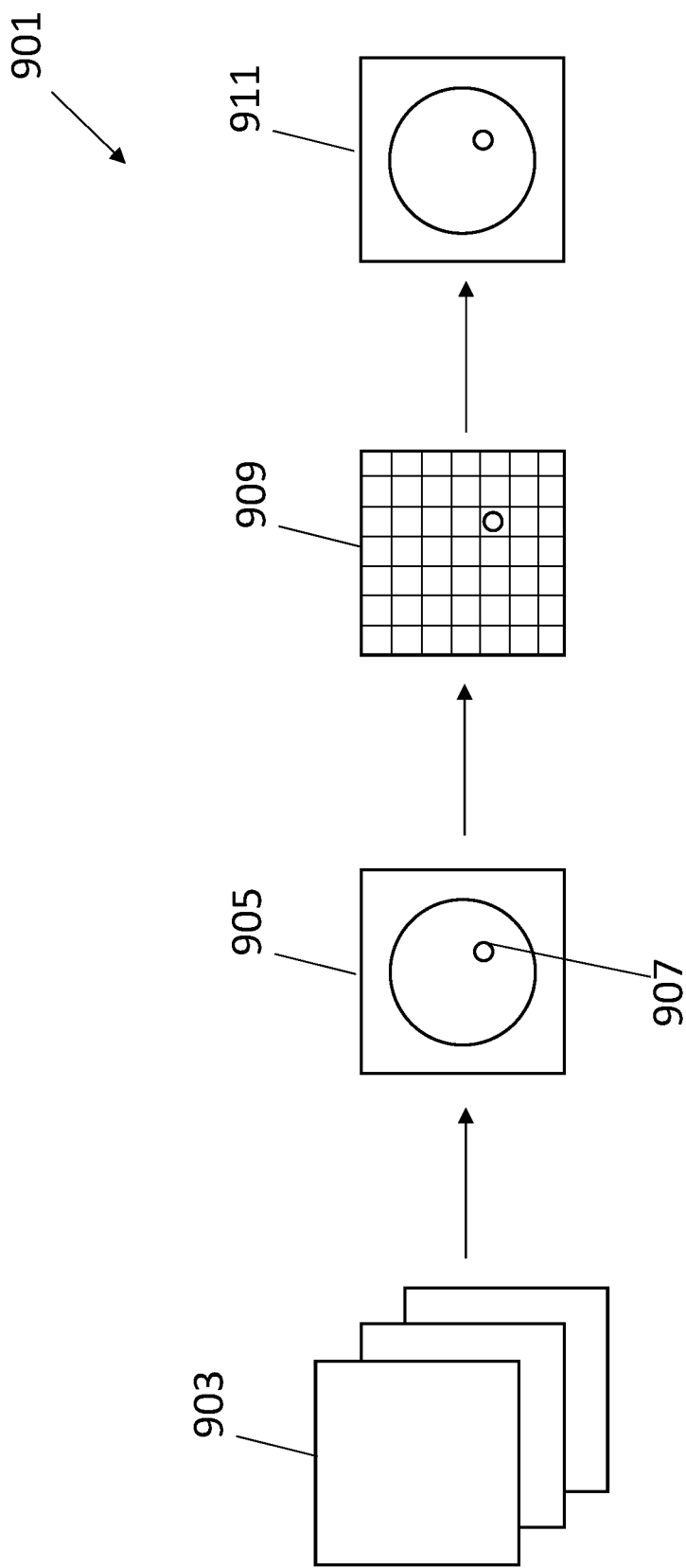
FIG. 9 illustrates a system for preparing a composite image in accordance with one or more embodiments.

FIG. 9 is a representation of a composite image compiler 901, according to at least one embodiment of the present disclosure. In one or more embodiments, the composite image compiler 901 is implemented within or in conjunction with the image quality assessor 108 discussed herein. For example, in one or more embodiments, the composite image compiler 901 may perform features described herein based on selectively identified images from video content identified by the image quality assessor 108 based on quality score(s) determined for the images and/or video content.

In one or more embodiments, the composite image compiler 901 may generate a composite image from video input 903. For example, a PCP may prepare a video of a target anatomical feature, such as a patient's eye. The composite image compiler 901 may analyze the video and prepare a composite image of all of the ocular features visible in the video input 903. To prepare the composite image, the composite image compiler 901 may review the individual frames of the video 903.

On a target frame 905, the composite image compiler 901 may identify an ocular feature 907. This includes identification of common features between frames and precise localization 909 of each feature in order to generate a transformation estimation layer for each frame. The system can then use patch extraction, non-linear mapping, and reconstruction to create super-resolution subcomponents within individual frames. Using the identified and localized features across at least two frames, two images may be stitched together to form a composite image 911. Because the images may be taken from a video, where the position and/or angular alignment may change from frame to frame, the two frames undergo an alignment process during stitching.

The alignment process may use a convolutional neural network (CNN) to accurately localize features. Training this neural network includes establishment of training datasets of eye exams (e.g., fundus exams) with features of interest already identified. Libraries, scripts, and datasets enable human based classification of components for CNN training purposes. It is also notable that the types of distortions in training videos and images should loosely match those expected in frames of the exam videos. After generation of the transformation estimation layers from these datasets, another CNN may be used to interpolate data from matching features across frames into a super-resolution composite image. Using edge estimation to minimize blocky artifacts in sub-pixel spaces, the system can achieve preliminary super resolution enhancement producing antialiasing effects and reducing artifacts of low quality captures. This enables the ophthalmic specialists performing the diagnostic to acquire a higher degree of accuracy and content from these image sets without the need for expensive capture hardware or advanced training, deskilling the capture process for primary care physicians.

Figure 10:
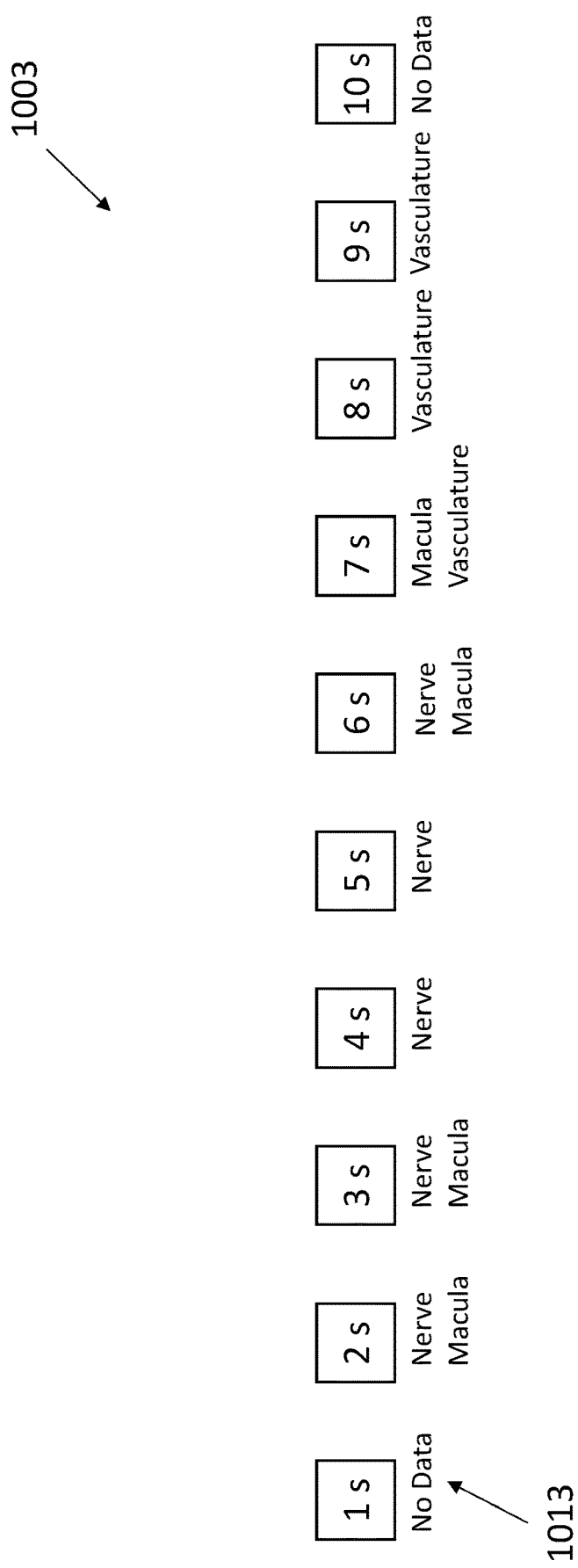
FIG. 10 illustrates a video input used to prepare a composite image in accordance with one or more embodiments.

FIG. 10 is a representation of a video input 1003 of an eye exam separated into time segments, according to at least one embodiment of the present disclosure. A composite image compiler may generate a composite image of the patient's eye using the frames from the video input 1003. In accordance with embodiments of the present disclosure, the composite image compiler may select one or more images from frames of the video input 1003 to use to generate the composite image.

In the embodiment shown, the images in the video input 1003 may include metadata 1013. The metadata may include the image quality score and any identified ocular features. In some embodiments, the composite image compiler may select the images used to generate the composite image using an image quality score generated by an image score assessor. In some embodiments, the composite image compiler may select the images based on the presence of one or more ocular features included in the image. In some embodiments, the composite image compiler may select images that include the same ocular features to be able to stitch the image together.

Many videos are taken with a frame rate of up to 60 frames per second, or more. A PCP recording the video may change the orientation of the ophthalmoscope slowly to maintain a high level of image clarity in the individual frames. This may result in frames that are adjacent in time, or frames proceeding earlier frames that may have little to no difference in the field of view captured. To reduce the processing resources used to prepare the composite image, the composite image compiler may select a sub-set of frames from the entirety of the video. The composite image compiler may generate the composite image by stitching images from the sub-set of frames together, rather than every single image from the input video. Reducing the number of images stitched together may reduce the processing resources used.

To select the stitching images, the composite image compiler may review the metadata 1013 tags of the images. As may be seen, at 1 second, the video may not include any ocular data, and all of these images may be discarded. From 2 seconds to 3 seconds, each frame of the video input 1003 may include images of the optic nerve and the macula. To reduce the processing resources, the composite image compiler may discard similar images. For example, the composite image compiler may discard images having a low or relatively low image quality score. In some examples, the composite image compiler may discard every other image, or may retain every 3 images, every 4 images, every 5 images, every 10 images, every 20 images, every 30 images, and so forth.

From 4 seconds to 5 seconds, the video input 1003 may include only images of the optic nerve. The composite image compiler may discard images that are adjacent in time. The composite image compiler may continue to discard images that are adjacent in time having a common feature visible. In this manner, the composite image compiler may use images from many portions of the video that include each of the identified ocular features. Furthermore, this may help to form a composite image that includes an entirety of each anatomical feature. For example, this may form a composite image that includes an entirety of the optic nerve, the macula, and the vasculature.

Figure 11:
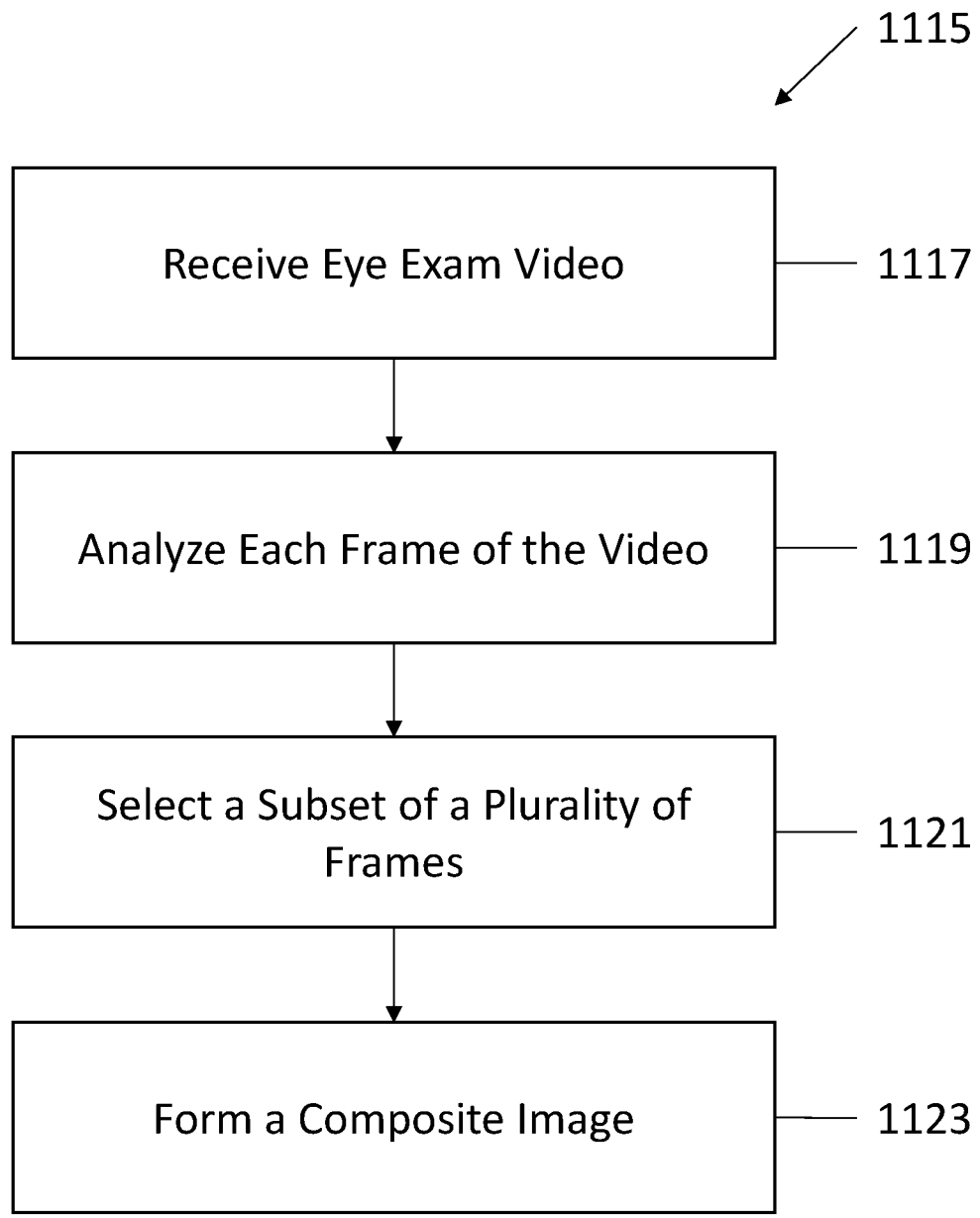
FIG. 11 illustrates a flowchart of a method for preparing a composite image in accordance with one or more embodiments.

FIG. 11 is a flowchart of a method 1115 for generating a composite image, according to at least one embodiment of the present disclosure. The method 1115 may include receiving an eye exam video from a mobile device prepared by a PCP at 1117. Each frame of the eye exam video may be analyzed for a presence of one or more ocular features at 1119. For example, as discussed herein, an image quality assessor may analyze the eye exam video for the ocular features. A subset of frames from the exam eye video may be selected based on the presence of the one or more ocular features at 1121. In some embodiments, the plurality of frames may not be adjacent in time to each other. For example, each frame of the plurality of frames may not be adjacent in time to any other frame from the selected plurality of frames. The composite image is formed using the plurality of frames at 1123.

In some embodiments, the generated composite image includes an entirety of the optic nerve and an entirety of the macula. In some embodiments, one of the plurality of frames is aligned with another of the plurality of frames to form the composite image. In some embodiments, because the frames are generated in sequential order, movement information may be determined based on the surrounding frames, including the previously discarded or not-selected frames. The movement information may be used to determine a motion between the plurality of frames based on previous motion in the eye exam video. In some embodiments, the method may further include applying at least one of shearing correction and luminance correction between the plurality of frames to generate the composite image.

Embodiments of the present disclosure may comprise or utilize a special purpose or general-purpose computer including computer hardware, such as, for example, one or more processors and system memory, as discussed in greater detail below. Embodiments within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., memory), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, embodiments of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed by a processor, cause a general-purpose computer, special purpose computer, or special purpose processing device to perform a certain function or group of functions. In some embodiments, computer-executable instructions are executed by a general-purpose computer to turn the general-purpose computer into a special purpose computer implementing elements of the disclosure. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the present disclosure can also be implemented in cloud computing environments. As used herein, the term "cloud computing" refers to a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In addition, as used herein, the term "cloud-computing environment" refers to an environment in which cloud computing is employed.

Figure 12:
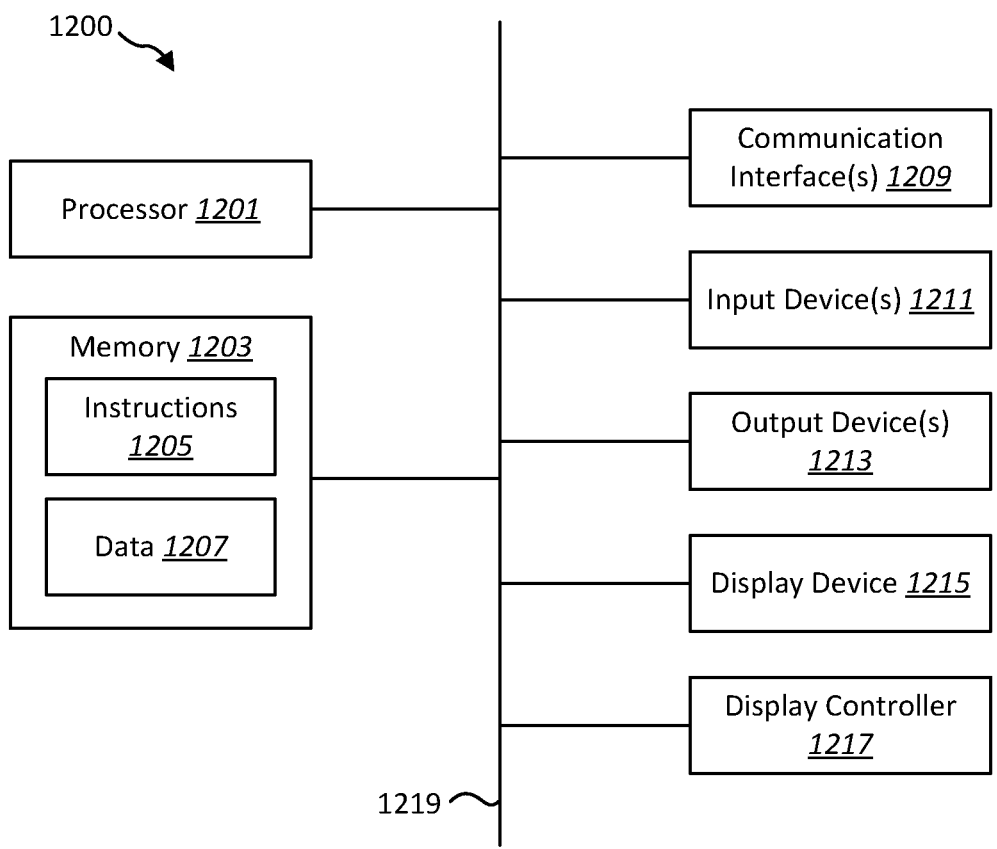
FIG. 12 illustrates certain components that may be included within a computer system.

FIG. 12 illustrates a block diagram of an example computing device 1200 that may be configured to perform one or more of the processes described above. One will appreciate that one or more computing devices, such as the computing device 1200 may represent the computing devices described above (e.g., image quality assessor 208). In one or more embodiments, the computing device 1200 may be a mobile device (e.g., a mobile telephone, a smartphone, a PDA, a tablet, a laptop, a camera, a tracker, a watch, a wearable device, etc.). In some embodiments, the computing device 1200 may be a non-mobile device (e.g., a desktop computer or another type of client device). Further, the computing device 1200 may be a server device that includes cloud-based processing and storage capabilities.

As shown in FIG. 12, the computing device 1200 can include one or more processor(s) 1202, memory 1204, a storage device 1206, input/output interfaces 1208 (or "I/O interfaces 1208"), and a communication interface 1210, which may be communicatively coupled by way of a communication infrastructure (e.g., bus 1212). While the computing device 1200 is shown in FIG. 12, the components illustrated in FIG. 12 are not intended to be limiting. Additional or alternative components may be used in other embodiments. Furthermore, in certain embodiments, the computing device 1200 includes fewer components than those shown in FIG. 12. Components of the computing device 1200 shown in FIG. 12 will now be described in additional detail.

In particular embodiments, the processor(s) 1202 includes hardware for executing instructions, such as those making up a computer program. As an example, and not by way of limitation, to execute instructions, the processor(s) 1202 may retrieve (or fetch) the instructions from an internal register, an internal cache, memory 1204, or a storage device 1206 and decode and execute them.

The computing device 1200 includes memory 1204, which is coupled to the processor(s) 1202. The memory 1204 may be used for storing data, metadata, and programs for execution by the processor(s). The memory 1204 may include one or more of volatile and non-volatile memories, such as Random-Access Memory ("RAM"), Read-Only Memory ("ROM"), a solid-state disk ("SSD"), Flash, Phase Change Memory ("PCM"), or other types of data storage. The memory 1204 may be internal or distributed memory.

The computing device 1200 includes a storage device 1206 includes storage for storing data or instructions. As an example, and not by way of limitation, the storage device 1206 can include a non-transitory storage medium described above. The storage device 1206 may include a hard disk drive (HDD), flash memory, a Universal Serial Bus (USB) drive or a combination these or other storage devices.

As shown, the computing device 1200 includes one or more I/O interfaces 1208, which are provided to allow a user to provide input to (such as user strokes), receive output from, and otherwise transfer data to and from the computing device 1200. These I/O interfaces 1208 may include a mouse, keypad or a keyboard, a touch screen, camera, optical scanner, network interface, modem, other known I/O devices or a combination of such I/O interfaces 1208. The touch screen may be activated with a stylus or a finger.

The I/O interfaces 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O interfaces 1208 are configured to provide graphical data to a display for presentation to a user. The graphical data may be representative of one or more graphical user interfaces and/or any other graphical content as may serve a particular implementation.

The computing device 1200 can further include a communication interface 1210. The communication interface 1210 can include hardware, software, or both. The communication interface 1210 provides one or more interfaces for communication (such as, for example, packet-based communication) between the computing device and one or more other computing devices or one or more networks. As an example, and not by way of limitation, communication interface 1210 may include a network interface controller (NIC) or network adapter for communicating with an Ethernet or other wire-based network or a wireless NIC (WNIC) or wireless adapter for communicating with a wireless network, such as a WI-FI. The computing device 1200 can further include a bus 1212. The bus 1212 can include hardware, software, or both that connects components of computing device 1200 to each other.

In the foregoing specification, the invention has been described with reference to specific example embodiments thereof. Various embodiments and aspects of the invention(s) are described with reference to details discussed herein, and the accompanying drawings illustrate the various embodiments. The description above and drawings are illustrative of the invention and are not to be construed as limiting the invention. Numerous specific details are described to provide a thorough understanding of various embodiments of the present invention.

The present invention may be embodied in other specific forms without departing from its spirit or essential characteristics. The described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A computer-implemented method for remotely collecting health information of a patient for a medical evaluation, comprising:
   receiving a captured video from a mobile device, the captured video including a plurality of video frames;
   applying a video assessment model to the plurality of video frames to determine a subset of video frames for use in a remote medical evaluation, including:
   generating an image quality score each video frame of the plurality of video frames based on at least a quality of each of the video frames of the plurality of video frames and a presence of predetermined ocular features within each of the video frames of the plurality of video frames; and
   identifying one or more frames of the plurality of the video frames to include in the subset of video frames based on one or more predetermined metrics, including at least the image quality score of the video frame;
   generating a video quality score for the captured video based at least in part on the image quality score of each of the video frames of the subset of video frames; and
   based on the video quality score, providing an indication to the mobile device whether the captured video is suitable for use in the remote medical evaluation.

2. The computer-implemented method of claim 1, wherein the captured video is an eye exam video.

3. The computer-implemented method of claim 2, wherein the image quality score of each of the video frames of the plurality of video frames is further based on a first score associated with the presence of a first ocular feature within each of the video frames and a second score associated with the presence of a second ocular feature within each of the video frames, wherein the image quality score of a particular video frame of the plurality of video frames is based at least in part on the first and the second scores.

4. The computer-implemented method of claim 3, wherein the video quality score is further based on the first score associated with the presence of the first ocular feature and the second score associated with the presence of the second ocular feature.

5. The computer-implemented method of claim 1, wherein the image quality score is based at least in part on an image clarity of each of the video frames of the plurality of video frames.

6. The computer-implemented method of claim 5, further including generating an evaluation video for use in the remote medical evaluation that includes at least the subset of video frames.

7. The computer-implemented method of claim 1, wherein the video assessment model includes an ensemble neural network that determines the image quality score for a given video frame.

8. The computer-implemented method of claim 7, wherein the ensemble neural network includes a plurality of neural networks that identifies the one or more predetermined ocular features.

9. The computer-implemented method of claim 1, wherein providing the indication to the mobile device occurs within ten seconds of receiving the captured video.

10. A computer-implemented method, comprising:
    receiving an eye exam video from a mobile device, the eye exam video including a plurality of video frames;
    analyzing each frame of the eye exam video for a presence of predetermined ocular features;
    analyzing each frame of the eye exam video based on one or more image quality metrics;
    determining an image quality score for each frame of the eye exam video based on an analysis for the presence of predetermined ocular features and based on the one or more image quality metrics;
    selecting a subset of video frames from the plurality of video frames of the eye exam video based on the presence of the one or more ocular features, wherein the subset of video frames includes two or more video frames from the plurality of video frames having timestamps that are non-adjacent to each other;
generating a video quality score based on the image quality score for each frame of the eye exam video; and
forming a composite image from the two or more video frames from the subset of video frames.

11. The computer-implemented method of claim 10, wherein the predetermined ocular features include at least one or more of an optic nerve, a macula, or vasculature.

12. The computer-implemented method of claim 11, wherein the composite image includes an entirety of the optic nerve and an entirety of the macula.

13. The computer-implemented method of claim 10, wherein forming the composite image includes aligning a first video frame from the two or more video frames with a second video frame from the two or more video frames.

14. The computer-implemented method of claim 13, wherein aligning the first video frame with the second video frame includes determining a motion between the first video frame and the second video frame based on a previous motion in the eye exam video.

15. The computer-implemented method of claim 10, further comprising applying at least one of shearing correction and luminance correction between respective frames of the subset of video frames.

16. A system for providing remote healthcare, comprising:
a processor; and
memory, the memory including instructions which, when accessed by the processor, cause the processor to:
  receive a captured video from a mobile device, the captured video including a plurality of video frames;
  apply a video assessment model to the plurality of video frames to determine a subset of video frames for use in a remote medical evaluation, the video assessment model including:
    generating an image quality score each video frame of the plurality of video frames based on at least a quality of each of the video frames of the plurality of video frames and a presence of predetermined ocular features within each of the video frames of the plurality of video frames; and
    identifying one or more frames of the plurality of the video frames to include in the subset of video frames based on one or more predetermined metrics, including at least the image quality score of the video frame;
  generating a video quality score for the captured video based at least in part on the image quality score of each of the video frames of the subset of video frames; and
  based on the video quality score, provide an indication to the mobile device whether the captured video is suitable for use in the remote medical evaluation.

17. The system of claim 16,
wherein the captured video is an eye exam video,
wherein the image quality score of each of the video frames of the plurality of video frames is further based on a first score associated with the presence of a first ocular feature within each of the video frames and a second score associated with the presence of a second ocular feature within each of the video frames, wherein the image quality score of a particular video frame of the plurality of video frames is based at least in part on the first and the second scores, and
wherein the video assessment model includes an ensemble neural network that determines the image quality score for each of the video frames.

18. The system of claim 16,
wherein determining the video quality score is further based on a first score associated with the presence of a first ocular feature and a second score associated with the presence of a second ocular feature.

19. The system of claim 16, wherein the indication to the mobile device includes an evaluation video for use in the remote medical evaluation that includes at least the subset of video frames.

* * * * *